(12) United States Patent
Hirschel et al.

(10) Patent No.: US 10,335,543 B2
(45) Date of Patent: Jul. 2, 2019

(54) INSERTION DEVICE FOR AN INFUSION SET

(71) Applicant: TecPharma Licensing AG, Burgdorf (CH)

(72) Inventors: Jürg Hirschel, Bern (CH); Mario Bernhard, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 151 days.

(21) Appl. No.: 14/811,023

(22) Filed: Jul. 28, 2015

(65) Prior Publication Data
US 2016/0030667 A1    Feb. 4, 2016

(30) Foreign Application Priority Data
Jul. 29, 2014   (CH) ........................................ 1157/14

(51) Int. Cl.
*A61M 5/158* (2006.01)
*A61B 17/34* (2006.01)
*A61M 25/06* (2006.01)

(52) U.S. Cl.
CPC .......... *A61M 5/158* (2013.01); *A61B 17/3403* (2013.01); *A61B 17/3415* (2013.01);
(Continued)

(58) Field of Classification Search
CPC .......... A61M 2005/1585; A61M 5/158; A61M 5/3287; A61M 25/0606;
(Continued)

(56) References Cited

U.S. PATENT DOCUMENTS 7,815,607 B2 * 10/2010 Rutti ..................... A61M 5/158 604/157
2002/0022855 A1 * 2/2002 Bobroff ................. A61M 5/158 606/185
(Continued)

FOREIGN PATENT DOCUMENTS

EP   1762259 A1   3/2007
EP   1631337 B1   10/2007
(Continued)

*Primary Examiner* — Kami A Bosworth
*Assistant Examiner* — Alexandra Lalonde
(74) *Attorney, Agent, or Firm* — Dorsey & Whitney LLP

(57) ABSTRACT

An insertion device for an infusion set includes an advancement unit or a sliding element for moving the infusion set along a central axis from a proximal position into a distal position, a retaining element for retaining the infusion set that includes a guide element, a base part for accommodating the retaining element that includes a mating guide element and a contact surface for placing the insertion device on an application point of a patient's body, and a head part arranged rotatably about a central axis in relation to the base part. Upon relative rotation between the head part and the base part in one direction, the guide element of the retaining element can be guided with the mating guide element provided on the base part such that the retaining element is movable along the central axis relative to the base part from the distal position into the proximal position.

22 Claims, 13 Drawing Sheets

US 10,335,543 B2
Page 2

(52) U.S. Cl.
CPC . *A61M 25/0606* (2013.01); *A61M 2005/1585* (2013.01); *A61M 2005/1587* (2013.01)

(58) Field of Classification Search
CPC ........... A61M 2005/14252; A61M 2005/1587; A61B 17/3403
See application file for complete search history.

(56) References Cited

U.S. PATENT DOCUMENTS

| | | | |
|---|---|---|---|
| 2005/0101912 A1 | 5/2005 | Faust et al. | |
| 2007/0093754 A1 | 4/2007 | Mogensen et al. | |
| 2008/0228144 A1 | 9/2008 | Liniger et al. | |
| 2008/0249472 A1 | 10/2008 | Liniger et al. | |
| 2008/0249473 A1 | 10/2008 | Rutti et al. | |
| 2009/0088722 A1 | 4/2009 | Wojcik | |
| 2009/0216215 A1 | 8/2009 | Thalmann et al. | |
| 2009/0287153 A1 | 11/2009 | Bresina et al. | |
| 2010/0022960 A1 | 1/2010 | Mejlhede et al. | |
| 2010/0152665 A1 | 6/2010 | Hasted | |
| 2010/0204653 A1 | 8/2010 | Gyrn | |
| 2010/0228226 A1 | 9/2010 | Nielsen | |
| 2010/0286714 A1* | 11/2010 | Gyrn | A61M 5/158 606/139 |
| 2011/0040254 A1 | 2/2011 | Gyrn et al. | |
| 2011/0295205 A1 | 12/2011 | Kaufmann | |
| 2012/0022344 A1 | 1/2012 | Kube | |
| 2012/0095406 A1 | 4/2012 | Gyrn et al. | |
| 2012/0143135 A1* | 6/2012 | Cole | A61M 5/158 604/164.04 |
| 2013/0079719 A1 | 3/2013 | Gyrn et al. | |
| 2013/0102965 A1 | 4/2013 | Teutsch | |
| 2013/0131467 A1 | 5/2013 | Deck | |
| 2013/0178798 A1 | 7/2013 | Pearson et al. | |
| 2013/0237918 A1 | 9/2013 | Gyrn | |
| 2014/0088509 A1* | 3/2014 | Sonderegger | A61M 25/02 604/157 |
| 2014/0088550 A1* | 3/2014 | Bene | A61M 5/158 604/506 |

FOREIGN PATENT DOCUMENTS

| | | |
|---|---|---|
| EP | 1970083 A1 | 9/2008 |
| EP | 2174680 A1 | 4/2010 |
| EP | 1970084 B1 | 8/2010 |
| EP | 2397181 A1 | 12/2011 |
| EP | 2399624 A1 | 12/2011 |
| EP | 2457606 A1 | 5/2012 |
| EP | 1487519 B1 | 6/2013 |
| WO | WO 1999033504 A1 | 7/1999 |
| WO | WO 2002/070037 A2 | 9/2002 |
| WO | WO 2003026728 A1 | 4/2003 |
| WO | WO 2005046780 A1 | 5/2005 |
| WO | WO 2005/049117 A2 | 6/2005 |
| WO | WO 2005065748 A1 | 7/2005 |
| WO | WO 2006061027 A2 | 6/2006 |
| WO | WO 2007031237 A1 | 3/2007 |
| WO | WO 2008014792 A1 | 2/2008 |
| WO | WO 2009010399 A1 | 1/2009 |
| WO | WO 2009103759 A1 | 8/2009 |
| WO | WO 2010112521 A1 | 10/2010 |
| WO | WO 2011012465 A1 | 2/2011 |
| WO | WO 2011014492 A1 | 2/2011 |
| WO | WO 2012123274 A1 | 9/2012 |
| WO | WO 2012131044 A1 | 10/2012 |
| WO | WO 2012134588 A1 | 10/2012 |
| WO | WO 2013182321 A1 | 12/2013 |
| WO | WO 2015032741 A1 | 3/2015 |

\* cited by examiner

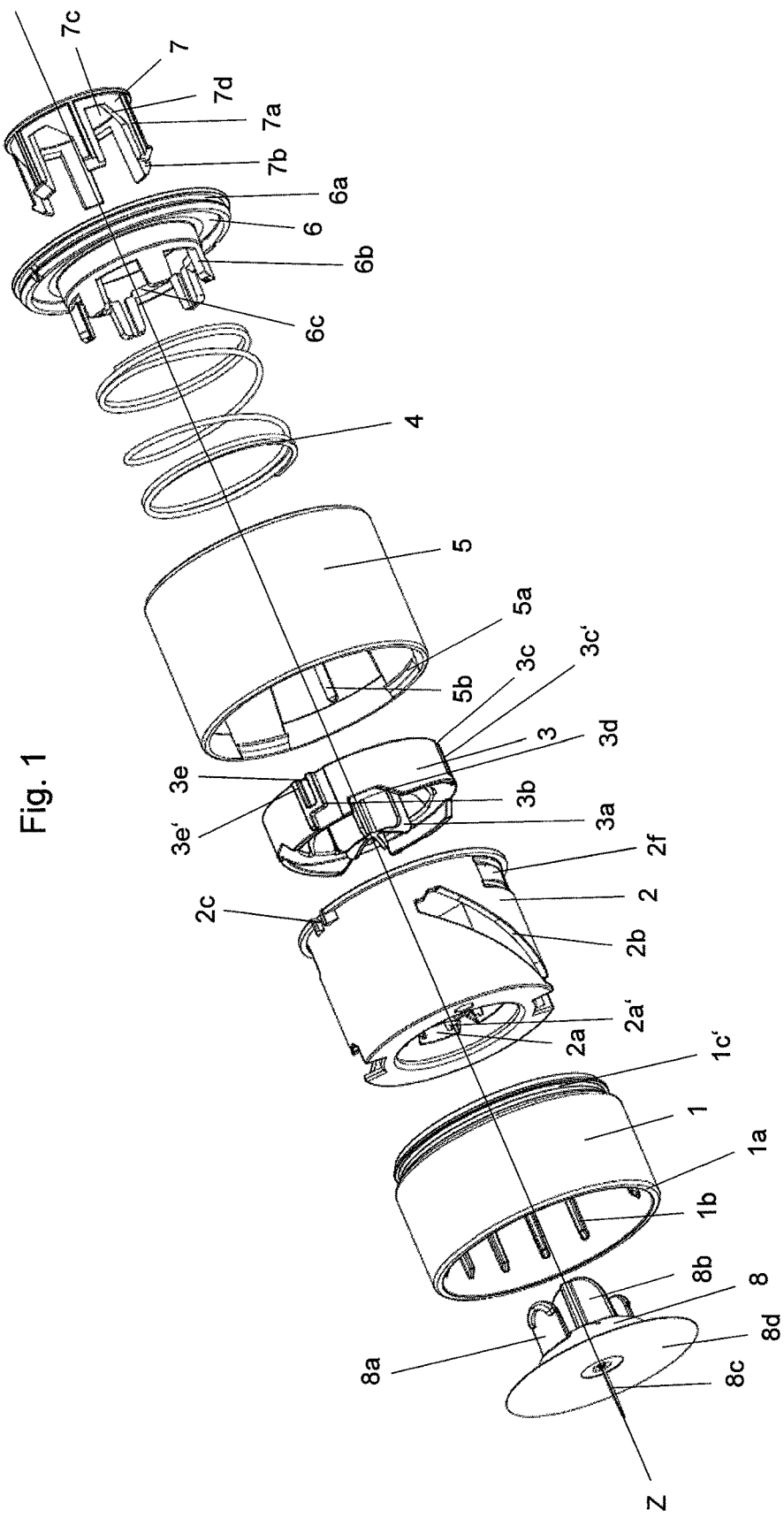

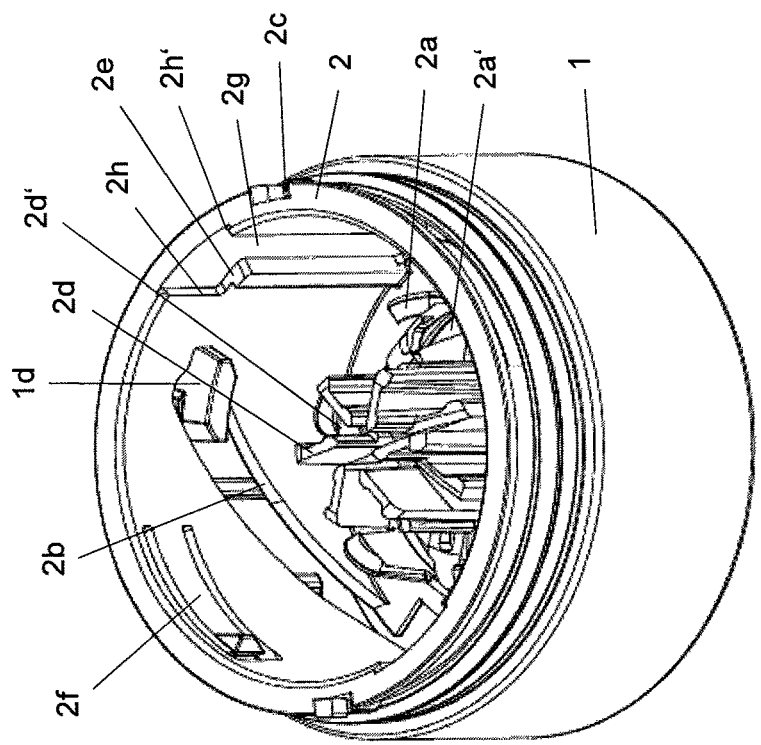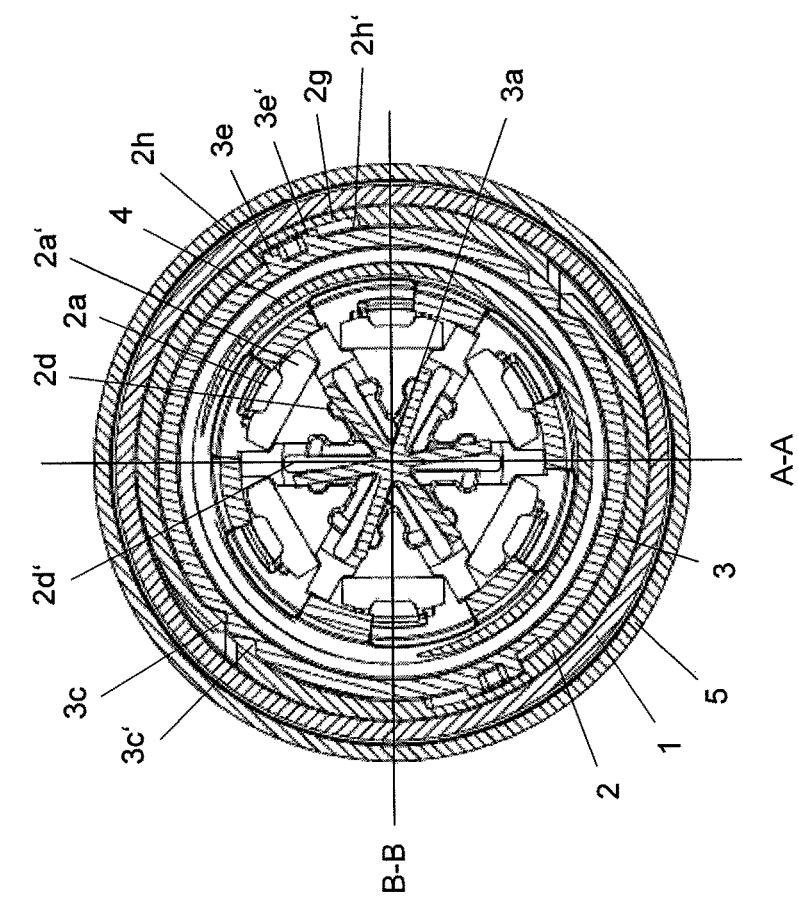

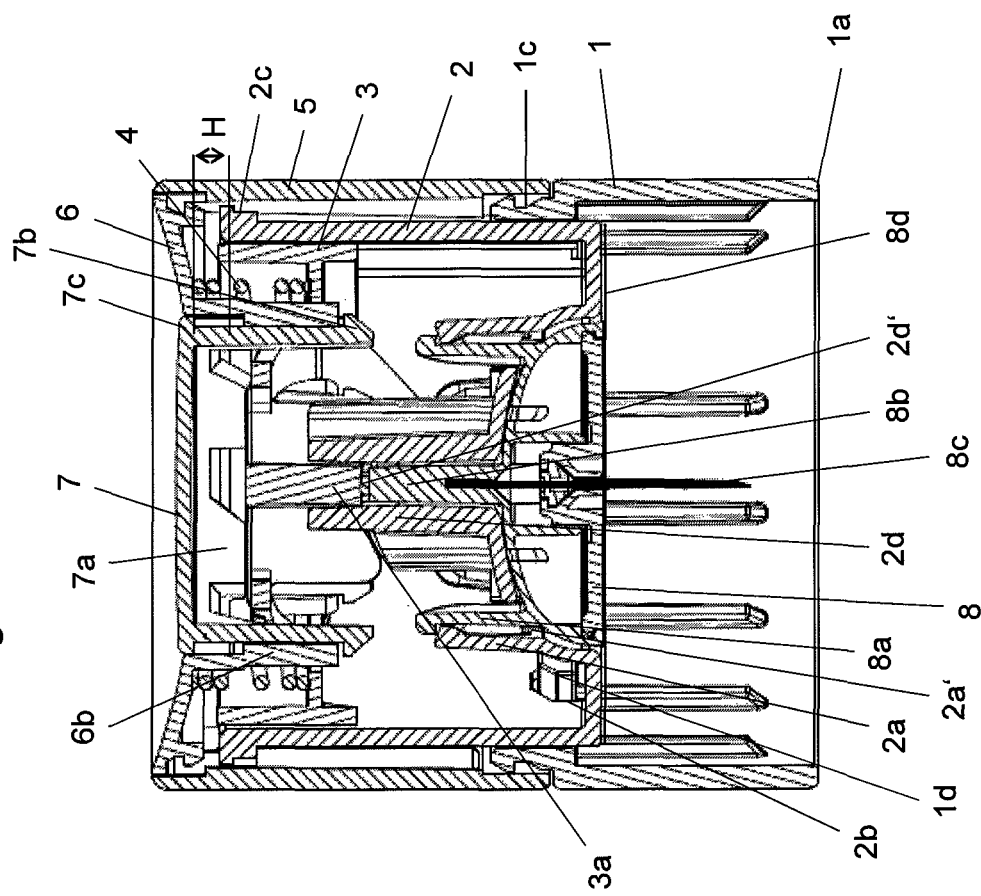
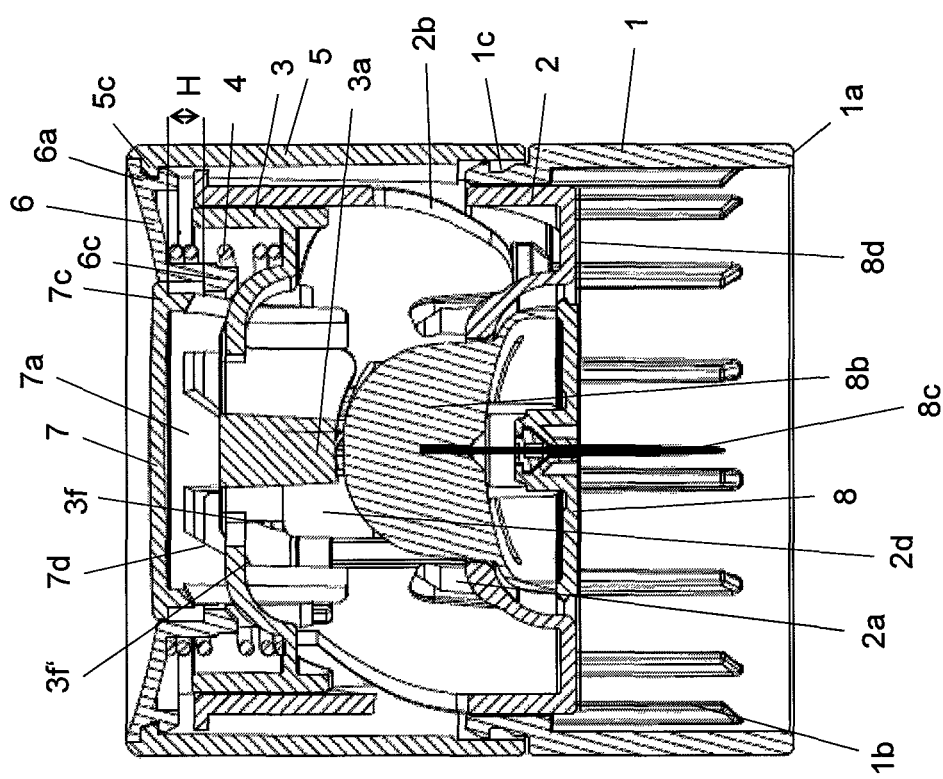

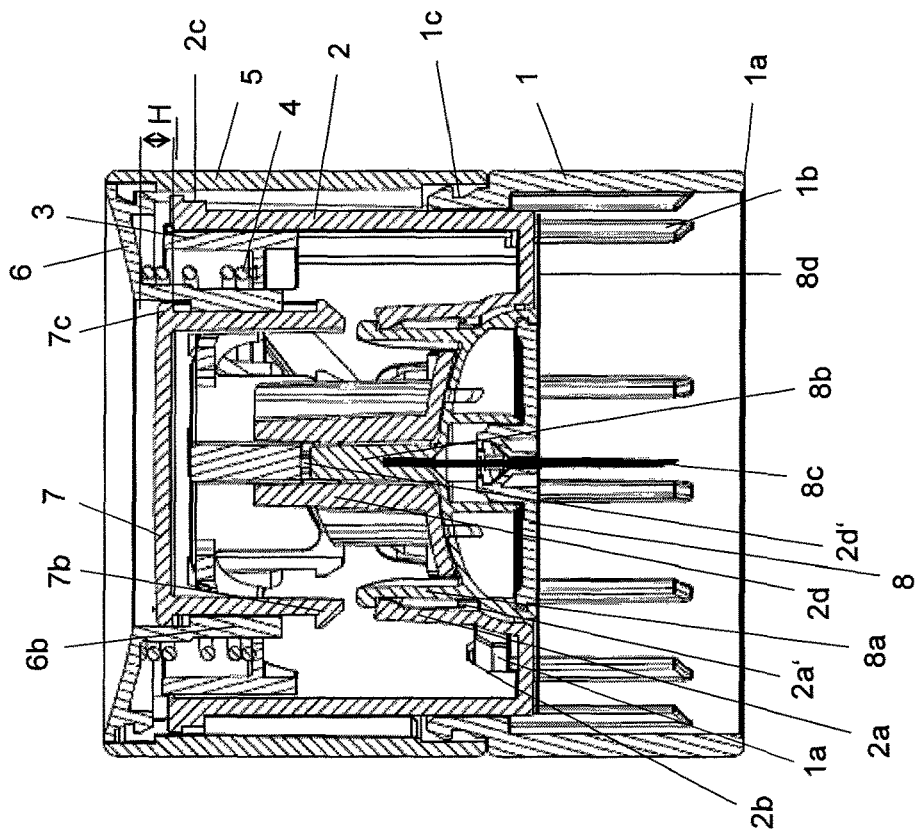
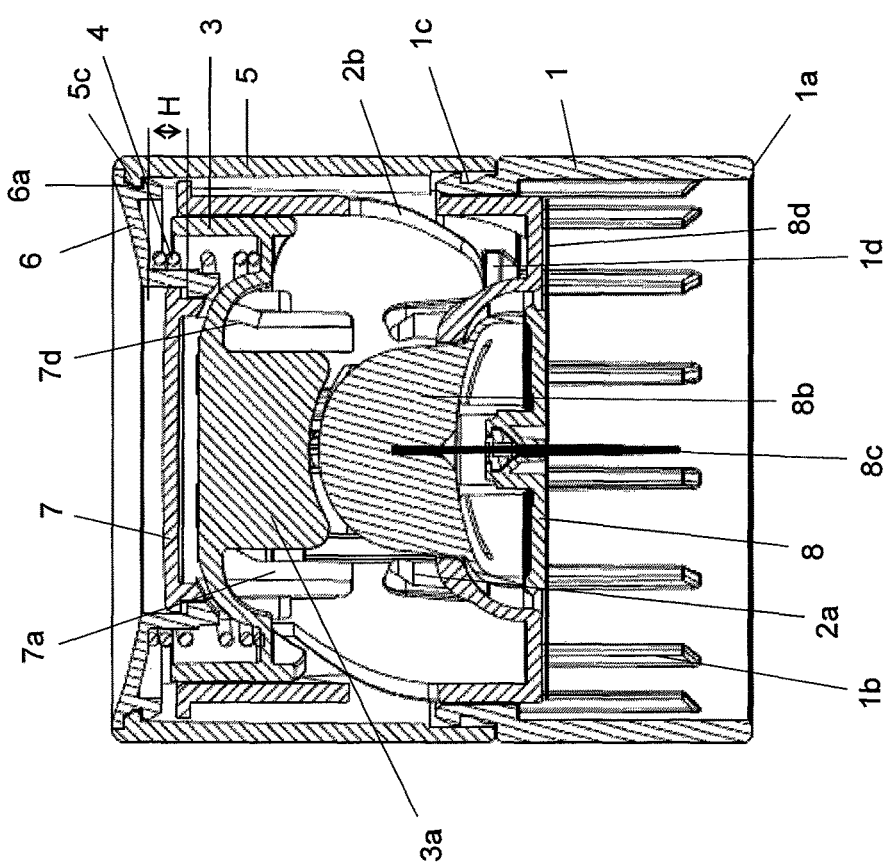

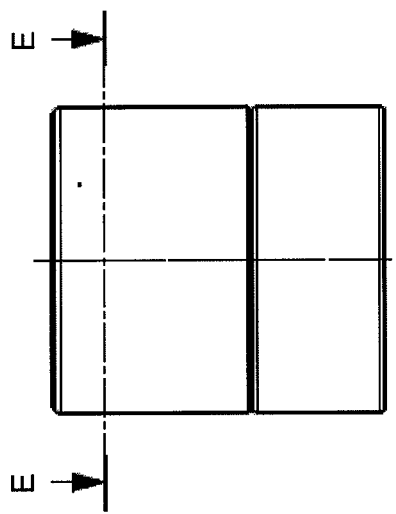
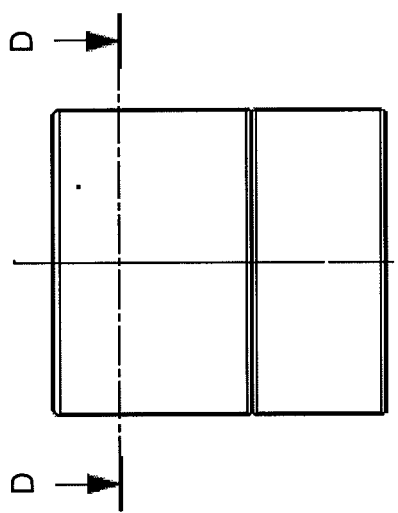
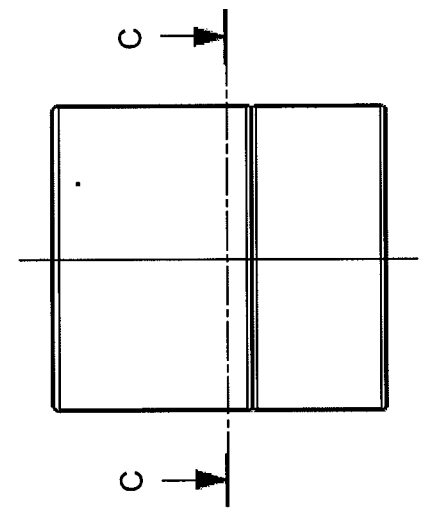

INSERTION DEVICE FOR AN INFUSION SET

CROSS-REFERENCE TO RELATED APPLICATIONS

This application claims priority to Swiss Patent Application No. 01157/14 filed Jul. 29, 2014, the contents of which are hereby incorporated by reference.

BACKGROUND

The present invention relates to an insertion device for an infusion set.

Infusion sets are known from WO02/070037A2 and from WO2005/049117A2, for example. Such infusion sets are used for insulin therapy, for example, wherein insulin is transported by the infusion pump into the body of a diabetic with the aid of an infusion set. The infusion set comprises a cannula, which is preferably placed directly under or in the skin by means of an insertion device or a puncturing aid, and held in place with an adhesive bandage.

An insertion device for such an infusion set is known from EP1487519B1 for example. The disadvantage with this insertion device is that, before the infusion set can be inserted into the device, an advancement unit for inserting the infusion set must be preloaded from a rest position into an operation-ready position.

Additional insertion devices or puncturing aids for an infusion set are known from EP1970084B1, EP1631337B1 and EP1970083A1. The insertion devices have in common the fact that the technology of these insertion devices is based on a lever mechanism; the insertion devices are consequently complicated in structure and have many components.

SUMMARY

A problem addressed by the present invention is therefore the provision of an insertion device that is easier to use and has a simpler structure. Another problem addressed by the present invention is the provision of an infusion set having such an insertion device with a simpler and safer procedure.

This problem is solved by the subject matter of the independent claims. Advantageous embodiments follow from the dependent claims.

Hereinafter, a proximal position of the insertion device means a position in which an advancement unit for conveying the infusion set into the skin is in a cocked position, and a distal position of the insertion device means a position in which the advancement unit for conveying the infusion set into the skin is in a relaxed position.

The invention relates to an insertion device for an infusion set, having an advancement unit for moving the infusion set from a proximal position into a distal position along a central axis (z). The insertion device may comprise a retaining element for holding the infusion set and a base part with a contact surface for placement of the insertion device on an application point on a patient's body, the base part being accommodated by the retaining element. The retaining element has at least one retaining arm for retaining the infusion set, preferably two or a multiple of two retaining arms. The retaining arm is preferably designed such that a retaining wing provided on the infusion set can be snapped into and out of the retaining arm. The retaining arm is preferably elastic. The insertion device further comprises a head part, which is arranged rotatably about a central axis (z) in relation to the base part. If there is a relative rotation between the head part and the base part in a first rotational direction, a guide element mounted on the retaining element can be guided with a mating guide element provided on the base part, the retaining element being movable along the central axis (z) relative to the base part from a distal position into a proximal position.

If there is a relative rotation between the head part and the base part in a second rotational direction, the guide element of the retaining element can be guided with the mating guide element provided on the base part, the retaining element being movable along the central axis (z) relative to the base part from the proximal position into the distal position. In other words, the retaining element can be moved along the (z) axis since the guide element of the retaining element is in a guiding engagement with the mating guide element provided on the base part.

Preferably the guide element of the retaining element is designed as a guide cam track and the mating guide element of the base part as a guide cam. Alternatively, the guide element of the retaining element is designed as a guide cam and the mating guide element of the base part as a guide cam track. A different guide element or a different mating guide element can also be provided, assuming that the guide element and the mating guide element are in a guiding engagement.

The retaining element is preferably connected rotationally fixedly to the head part. The head part can rotate along with the retaining element relative to the base part in a first direction and/or a second direction.

A cover can additionally be rotationally fixedly connected to the head part. Alternatively, the cover can be integrally formed with the head part. The head part is preferably accommodated on the cover at the proximal end.

The advancement unit can preferably have an elastic means and a sliding element. If there is a relative rotation between the head part and the base part in the first rotational direction, the elastic means can be cocked, and the elastic means can be relaxed if there is a relative rotation between the head part and the base part in the second rotational direction. The elastic means can be supported on the sliding element and on the head part or the cover part, or alternatively on the base part. The elastic means can therefore be designed as a compression spring or a tensile spring.

In the proximal position of the advancement unit, the sliding element can preferably be rotatable from a first position into a second position, wherein the sliding element can be retained by the retaining element in the first position and the sliding element can be released by the retaining element in the second position, so that the sliding element can be moved axially along the central axis (z) relative to the retaining element.

In the distal and proximal position of the advancement unit, the sliding element is preferably arranged offset from the retaining element by an angle of rotation, preferably by an angle of rotation of approximately 10°. A different angle of rotation can also be provided.

The sliding element can have a striking element for knocking the infusion set out of the retaining element, or can be constructed as a sleeve-like striking element.

The cover preferably accommodates a pushbutton. The pushbutton can be displaceable by an actuation stroke (H) along the central axis (z). In addition, the pushbutton can be designed such that when the pushbutton is pressed by the amount of the actuation stroke (H), the sliding element can be rotated about the central axis (z) relative to the retaining element by an angle of rotation into the second position.

The invention additionally relates to an insertion device for an infusion set that includes a base part comprising a mating guide element and a contact surface configured to be placed on an application point of a patient's body; a head part rotatably coupled to the base part such that the two are rotatable relative to one another about a central axis; a sliding element movable axially within an interior of the base part and the head part, the sliding element for moving the infusion set along the central axis; and an actuator for causing the sliding element to move along the central axis from a loaded position into an insertion position. Relative rotation between the head part and the base part in a first rotational direction causes a guide element associated with the sliding element to be guided with the mating guide element of the base part such that the sliding element moves along the central axis relative to the base part from an initial position into the loaded position. In the loaded position, the sliding element is rotatable about the central axis from a first position into a second position, the sliding element prevented from axial movement in the first position and movable axially relative to the retaining element in the second position. Upon actuating the actuator in the loaded position, the sliding element rotates from the first position into the second position and the sliding element is caused to move axially into the insertion position such that the infusion set is inserted at the application point.

The invention further relates to a method for inserting an infusion set by using an insertion device according to one of the preceding claims, comprising the following steps:

performing a relative rotational movement between the head part (5) and the base part (1) in a second rotational direction inserting an infusion set into a retaining element (2)

performing a relative rotational movement between the head part (5) and the base part (1) in a first rotational direction placing the insertion device on an application point on the body of a patient triggering the insertion device by pressing a cover (6) or a pushbutton (7)

removing the insertion device from the application point on the patient's body.

BRIEF DESCRIPTION OF THE DRAWINGS

FIG. 1 shows an exploded view of one embodiment of an insertion device.

FIG. 2c shows a cross-sectional view of the embodiment of the insertion device in the initial position according to FIG. 2a, the cross-sectional view corresponding to the section line C-C drawn in FIG. 7.

FIG. 2d, wherein the retaining element (2) and the base part (1) are visible, shows a detailed view of the embodiment of the insertion device in the initial position according to FIG. 2a.

FIG. 2e, wherein the head part (5), the base part (1) and the sliding element (3) are visible, shows a detailed view of the embodiment of the insertion device in the initial position according to FIG. 2a.

FIG. 2f, wherein the head part (5), the base part (1) and the retaining element (2) are visible, shows a detailed view of the embodiment of the insertion device in the initial position according to FIG. 2a.

FIG. 4a shows a longitudinal sectional view of the embodiment of the insertion device in a loaded position, the longitudinal sectional view corresponding to the section line A-A drawn in FIG. 4c.

FIG. 4b shows a longitudinal sectional view of the embodiment of the insertion device in the loaded position according to FIG. 4a, the longitudinal sectional view corresponding to the section line B-B drawn in FIG. 4c.

FIG. 4d, wherein the retaining element (2) and the base part (1) are visible, shows a detailed view of the embodiment of the insertion device in the loaded position according to FIG. 4a.

FIG. 4e, wherein the head part (5), the base part (1) and the retaining element (2) are visible, shows a detail view of the embodiment of the insertion device in the loaded position according to FIG. 4a.

FIG. 5a shows a longitudinal sectional view of the embodiment of the insertion device in a triggered position, the longitudinal sectional view corresponding to the section line A-A drawn in FIG. 5c.

FIG. 5b shows a longitudinal sectional view of the embodiment of the insertion device in the triggered position according to FIG. 5a, the longitudinal sectional view corresponding to the section line B-B drawn in FIG. 5c.

FIG. 7 shows a representation of the insertion device with section line C-C drawn in.

FIG. 8 shows a representation of the insertion device with section line D-D drawn in.

FIG. 9 shows a representation of the insertion device with section line E-E drawn in.

DETAILED DESCRIPTION

Figures 2A, 2B:
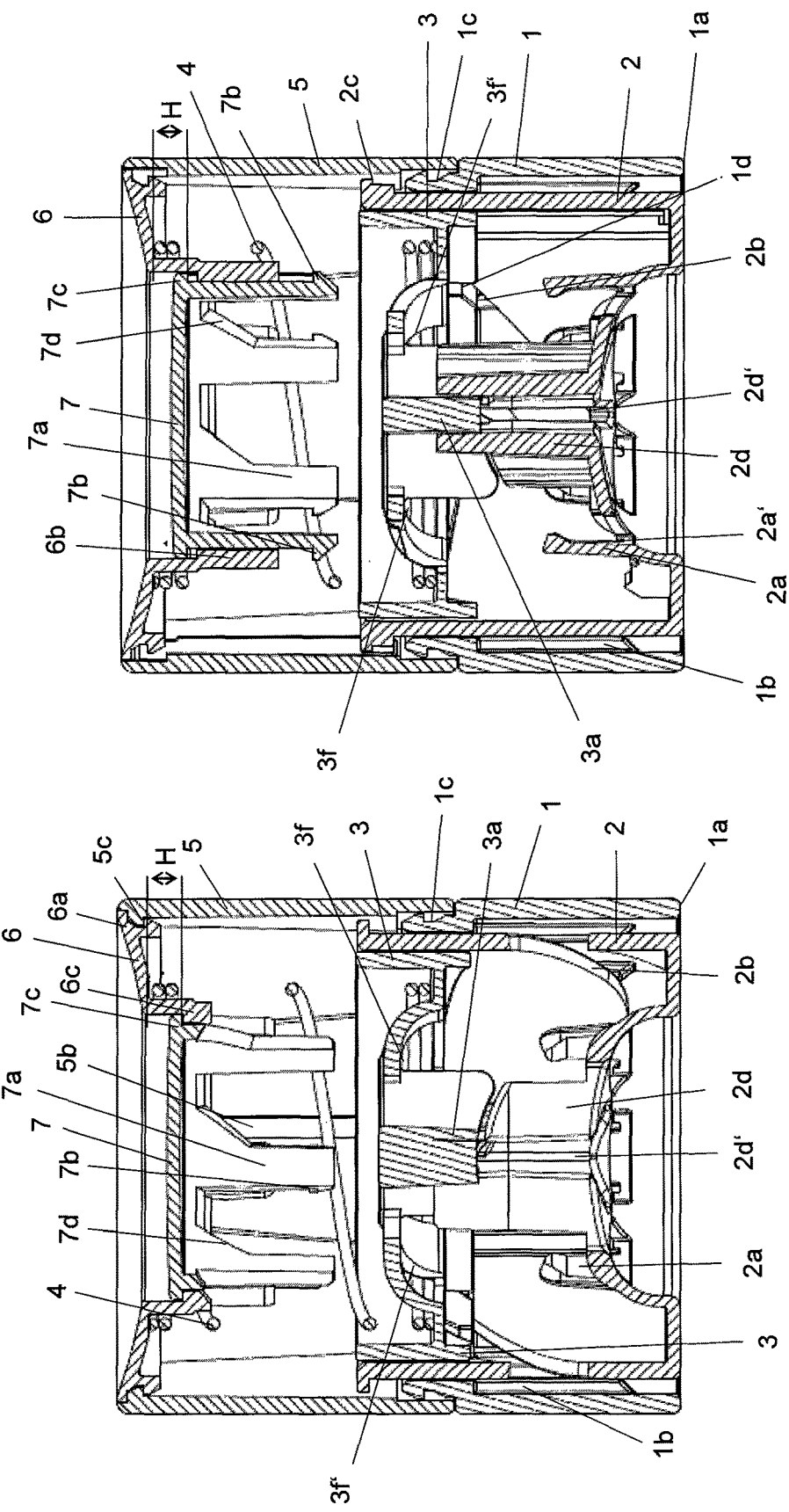
FIG. 2a shows a longitudinal sectional view of the embodiment of the insertion device in an initial position, the longitudinal sectional view corresponding to the section line A-A drawn in FIG. 2c.
FIG. 2b shows a longitudinal sectional view of the embodiment of the insertion device in the initial position according to FIG. 2a, the longitudinal sectional view corresponding to the section line B-B drawn in FIG. 2c.

FIG. 1 shows an exploded view of one embodiment of an insertion device according to the invention. The injection device comprises a retaining element (2) for holding an infusion set (8), wherein the infusion set (8) can comprise a cannula (8c) for puncturing the skin of a patient and an adhesive bandage (8d) for securing the infusion set on the skin of the patient. For this purpose, the retaining element (2) comprises at least two retaining arms (2a in FIG. 2a or FIG. 2f for example) wherein the at least two elastic retaining arms (2a in FIG. 2a or FIG. 2f for example) are arranged radially offset from one another by 180°, or a multiple of two elastic retaining arms (2a in FIG. 2a or FIG. 2f for example), in the present example six retaining arms (2a in FIG. 2a or FIG. 2f for example). The retaining arms (2a in FIG. 2a or FIG. 2f for example) are designed such that two retaining wings (8a) arranged on the infusion set (8) can snap into and out of the retaining arms (2a in FIG. 2a or FIG. 2f for example). The retaining element (2) further comprises at least two retaining slots (2a' in FIG. 2b or FIG. 2f for example), wherein the at least two retaining slots (2a' in FIG. 2b or FIG. 2f for example) are arranged radially offset by 180° from one another, or a multiple of two retaining slots (2a' in FIG. 2b or FIG. 2f for example), in the present example six retaining slots (2a' in FIG. 2b or FIG. 2f for example), by which the two retaining wings provided (8a) on the infusion set (8) can be introduced and removed. In order for the infusion set (8) to be guided in the retaining element (2), the retaining element (2) has a guide slot (2d' in FIG. 2a or FIG. 2f for example) on the distal end, in the present example three retaining slots (2d' in FIG. 2a or FIG. 2f for example). Guide ridges (2d in FIG. 2a or FIG. 2d for example) projecting in the proximal direction are provided along the guide slot (2d' in FIG. 2a or FIG. 2f for example), so that a retaining tab (8b) positioned on the infusion set (8) can be guided in the retaining element (2). The guide ridge (2d in FIG. 2d for example) of the retaining element (2) can have different lengths, the guide ridge (2d in FIG. 2d for example) or a pair of guide ridges (2d in FIG. 2d for example) being designed such that a guidance of the infusion set (8) and a relative rotation between the sliding element (3) and the retaining element (2) can be guaranteed. The insertion device further comprises a head part (5) and a base part (1), wherein the base part (1) has accommodated the retaining element (2). The base part (1) comprises a contact surface (1a) for placing the insertion device on an application point on the patient's body. Longitudinal ribs (1b) for axially guiding the retaining element (2) along a central axis (z) are arranged on the inner circumferential surface of the base part (1). An annular groove (1c') is provided at the proximal end and on the outer circumferential surface of the base part (1). A snapper or preferably a plurality of snappers (5a), at least four snappers (5a) in the present example, are positioned at the distal end and on the inner circumferential surface of the head part (5). The snappers (5a) of the head part (5) are snapped into the annular groove (1c') of the base part (1) in such a manner that the head part (5) can rotate relative to the base part (5). The retaining element (1) has a guide element in the form of a guide cam track (2b) or slot, which is engaged with a mating guiding element in the form of guide cam (1d in FIG. 2b for example) that is provided on the base part (1). If there is a relative rotation between the head part (5) and the base part (1) in a first rotational direction, the guide cam track (2b) of the retaining element (2) can be guided with the guide cam (1d in FIG. 2b for example) provided on the base part (1), wherein the retaining element (2) can be moved along the central axis (z) relative to the base part (1) from a distal position into a proximal position. The retaining element (2) can be guided due to, or by means of, the guide pair (1d, 2b). If there is a relative rotation between the head part (5) and the base part (1) in a second rotational direction, the guide cam track (2b) of the retaining element (2) can likewise be guided with the guide cam (1d in FIG. 2b for example) provided on the base part (1), wherein the retaining element (2) can be moved along the central axis (z) relative to the base part (1) from the proximal position into a distal position. The retaining element (2) is rotationally fixedly and axially movably connected to the head part (5). For this purpose, the retaining element (2) comprises a groove (2c) on the outer circumferential surface, the groove being engaged with a longitudinal rib (5b) provided on the inner circumferential surface of the head part (5). The insertion device further comprises an advancement unit. The advancement unit comprises an elastic means in the form of a compression spring (4) and a sliding element (3). The compression spring (4) is mounted between the sliding element (3) and a cover (6) such that it can be cocked. The cover (6) is axially fixedly connected to the head part (5) via a snap connection. For this purpose, the cover (6) has, at the proximal end thereof, a cover groove (6a in FIG. 2a for example), which is engaged with an annular ridge (5c in FIG. 2a for example) provided on the head part (5). The sliding element (3) has a striking element (3a) for knocking the infusion set (8) out of the insertion device via the retaining tab (8b). On the sliding element (3), a sliding element stop (3b) is provided, which can come into stopping contact with a retaining element stop (2e in FIG. 2d for example) provided on the inner circumferential surface of the retaining element (2). Due to the stopping contact between the sliding element stop (3b) and the retaining element stop (2e in FIG. 2d for example), the sliding element (3) is axially fixedly connected to the retaining element (2). In order that the sliding element (3) cannot come out of stopping contact with the retaining element (2), a snapper (2f) provided on the inner circumferential surface of the retaining element (2) can snap into a first longitudinal groove (3c) provided on the outer circumferential surface of the sliding element (3). In addition, a stopping contact can be provided between a first sliding element ridge (3e) provided on the sliding element (3) and a first retaining element ridge (2h in FIG. 2d for example) positioned on the retaining element (2), in order to limit a relative rotation between the sliding element (3) and the retaining element (2) in a first rotational direction. In order to limit a relative rotation between the sliding element (3) and the retaining element (2) in a second rotational direction, a stopping contact is provided between a second sliding element ridge (3e') provided on the sliding element (3) and a second retaining element ridge (2h in FIG. 2d for example) placed on the retaining element (2). If the second sliding element ridge (3e') is in stopping contact with the second retaining element ridge (2h in FIG. 2d for example), the sliding element (3) is out of stopping contact with the retaining element (2), so that the sliding element (3) is axially movable relative to the retaining element (2). For this purpose, the retaining element (2) has a guide groove (2g in FIG. 2d for example) on the inner circumferential surface, wherein the sliding element stop (3b) with the first and second sliding element ridges (3e, 3e') can slide along the guide groove (2g). The snapper (2f) of the retaining element (2) can lie in a second longitudinal groove (3c') of the sliding element (3), the second longitudinal groove (3c') being arranged radially offset from the first longitudinal groove (3c) of the sliding element. The sliding element (3) further comprises a control cam track (3d), which can come into guiding engagement with the guide cam (1d in FIG. 2b for example) of the base part (1). In case of a relative rotation of the head part (5) and the base part (1), the sliding element (3) can be rotated relative to the retaining element (2) via the guide cam (1d in FIG. 2e for example) of the base part (1) and via the control cam track (3d in FIG. 2e for example) of the sliding element (3). The sliding element (3) moves relative to the retaining element (2) from a first position to a second position. The guide cam track (2b) of the retaining element (2), the guide cam (ld in FIG. 2b for example) of the base part (1) and the control cam track (3d in FIG. 2e for example) of the sliding element (3) are designed and arranged such that the sliding element (3) can be rotated relative to the retaining element (2). The angle of rotation between the sliding element (3) and the retaining element (2) can preferably be approximately 10°. Other angles of rotation can also be provided, for example, 12° or 15°. The insertion device further comprises a pushbutton (7), which is accommodated by the cover (6). The pushbutton (7) has a snap arm (7a), six snap arms (7a) in the present example, projecting in the distal direction. The snap arms (7a) are in sliding contact with cover ridges (6b) provided on the cover (6). A snap hook (7b) formed on each snap arm (7a) forms a stop together with the distal end of the cover ridge (6b), so that the relative axial movement of the pushbutton (7) relative to the cover (6) in the proximal direction is limited. The relative axial movement in the distal direction of the pushbutton (7) relative to the cover (6) is formed between a pushbutton disc (7c) provided at the proximal end of the pushbutton (7) and a cover shoulder (6c) formed at the proximal end of the cover (6). The pushbutton (7) further comprises a pushbutton incline (7d), which can cooperate with a sliding element edge (3f in FIG. 2e for example) provided on a sliding element opening (3f in FIG. 2e for example) of the sliding element (3) in order to move the pushbutton (7) axially relative to the cover (6).

Figure 2E:
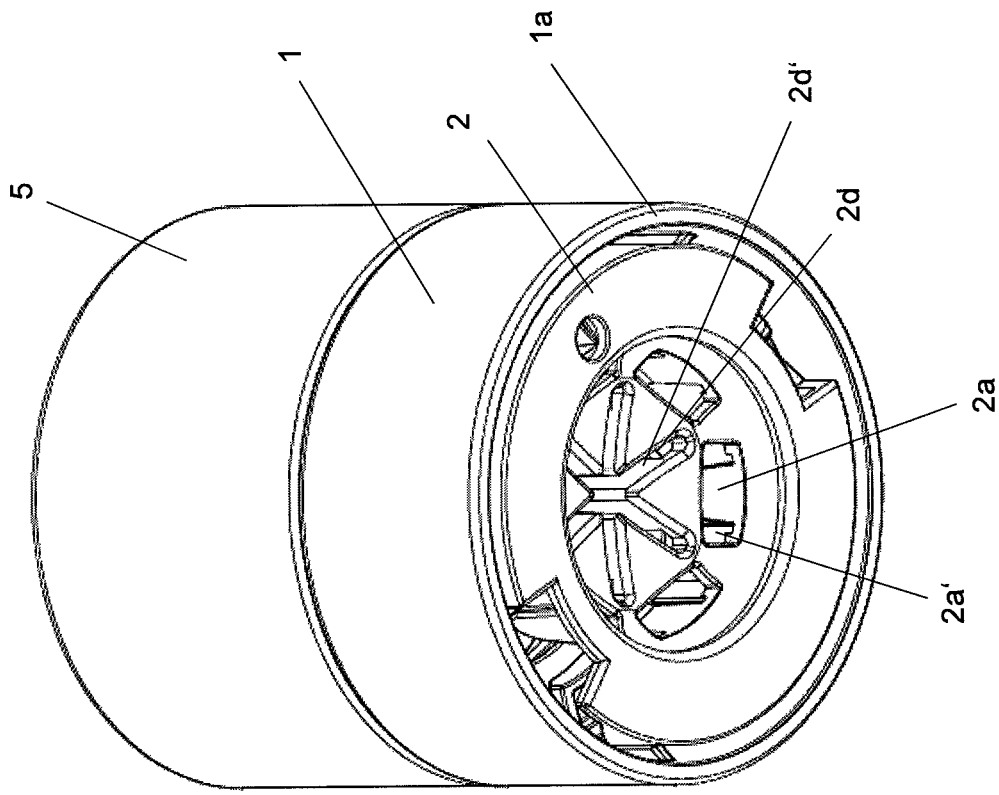
Figure 2F:
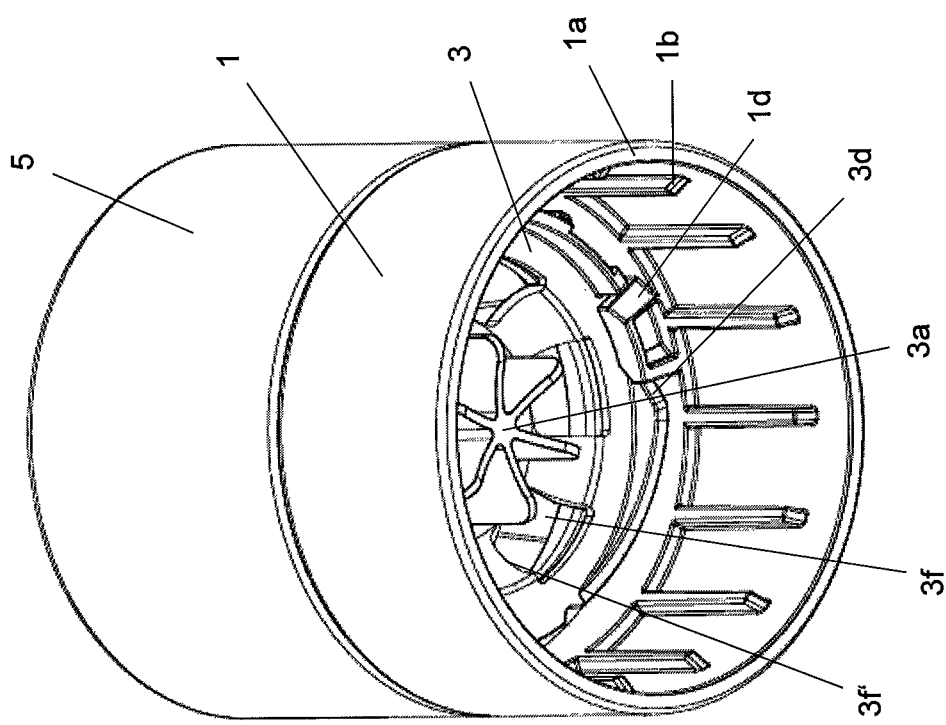

FIG. 2a represents a longitudinal sectional view of the embodiment of the insertion device in an initial position, the longitudinal sectional view corresponding to the section line A-A drawn in FIG. 2c. FIG. 2b shows the insertion device according to FIG. 2a, the longitudinal sectional view corresponding to the section line B-B drawn in FIG. 2c. The retaining element (2), the pushbutton (7) and the advancement unit (3, 4) are located in the distal position wherein no infusion set has been inserted into the insertion device. As can be seen in FIG. 2d, the guide cam of (1d) of the base part (1) is in stopping contact with the proximal end of the guide cam track (2b) of the retaining element (2). The pushbutton disc (7c) of the pushbutton (7) is in stopping contact with the cover ridge (6b) of the cover (6). The sliding element stop (3b) of the sliding element rests against the retaining element stop (2e) of the retaining element (2), so that the sliding element (3) is axially fixedly connected to the retaining element (2). The snapper (2f) of the retaining element (2) protrudes into the first longitudinal groove (3c) of the sliding element (3), so that the sliding element (3) cannot come out of stopping contact with the retaining element (2) on its own. The compression spring (4) is mounted between the cover (6) and the sliding element (3) in such a manner that the sliding element (3) and the retaining element (2) are held in the distal position. The compression spring (4) can be relaxed, or preferably, cocked. The snap arm (7a) of the pushbutton (7) protrudes through the sliding element opening (3f) of the sliding element (3). The pushbutton disc (7a) of the pushbutton (7) rests against the cover shoulder (6c) of the cover (6).

Figure 3A:
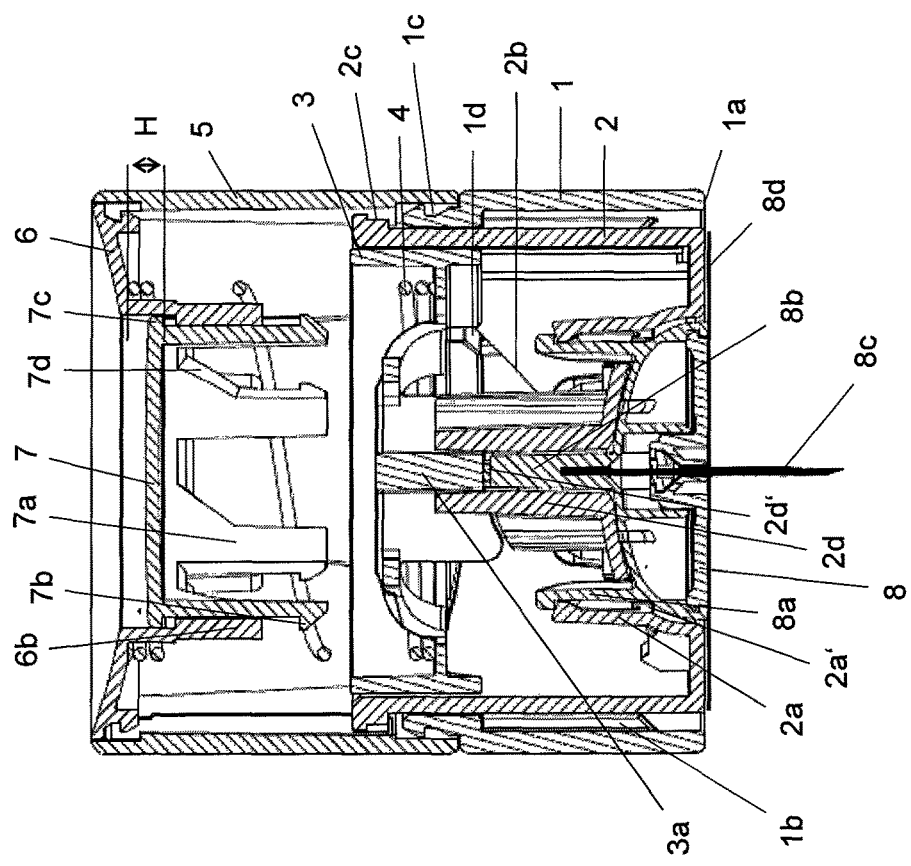
FIG. 3a shows a longitudinal sectional view of the embodiment of the insertion device with an inserted infusion set, the longitudinal sectional view corresponding to the section line A-A drawn in FIG. 2c.
Figure 3B:
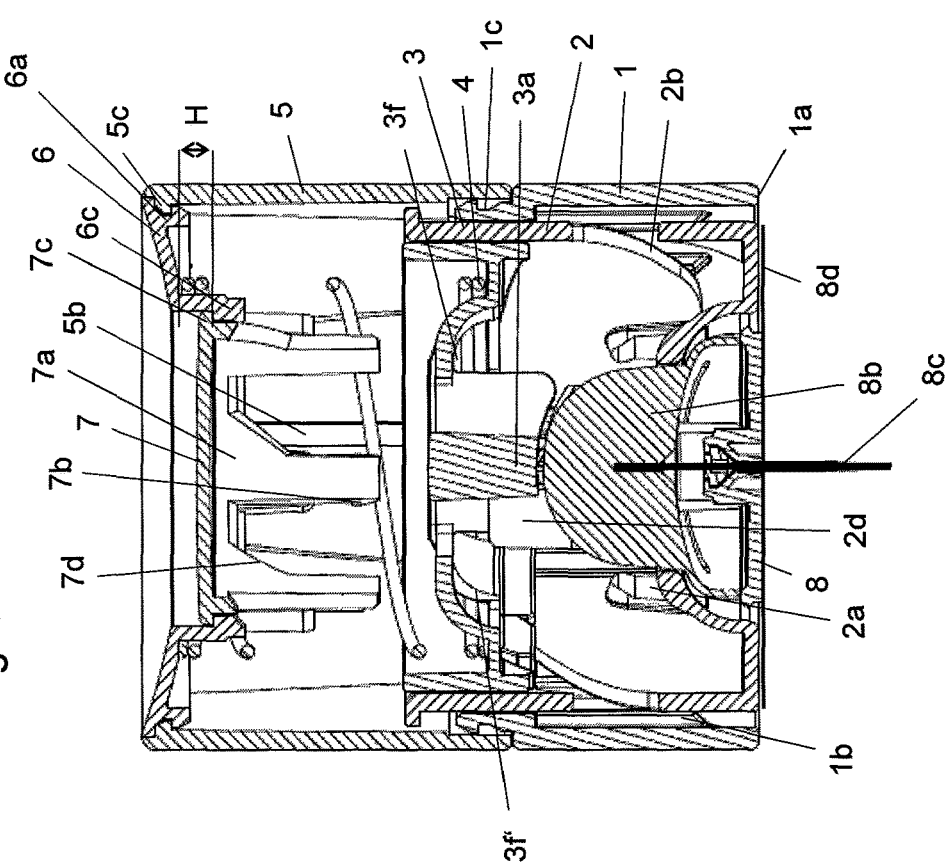
FIG. 3b shows a longitudinal sectional view of the embodiment of the insertion device with the infusion set inserted according to FIG. 3a, the longitudinal sectional view corresponding to the section line B-B drawn in FIG. 2c.

FIG. 3a shows a longitudinal sectional view of the embodiment of the insertion device with the inserted infusion set, the longitudinal sectional view corresponding to the section line A-A drawn in FIG. 2c. FIG. 3b shows the insertion device according to FIG. 3a, the longitudinal sectional view corresponding to the section line B-B drawn in FIG. 2c. The patient guides the infusion set (8) with the retaining tab (8b) through the guide slot (2d') of the retaining element (2), wherein the retaining tab (8b) is guided by the guide ridges (2d) of the retaining element (2) so that the infusion set (8) can be introduced into the insertion device. The retaining wings (8a) of the infusion set (8) penetrate through the retaining slots (2a') of the retaining element (2) and snap into the retaining arms (2a) of the retaining element (2). The infusion set (8) has been inserted into the insertion device. The sliding element (3), more particularly the striking element (3a) of the sliding element (3), and the infusion set (8), more particularly the retaining tab (8b) of the intrusion set (8), can thus come into stopping contact, or preferably, not into stopping contact, i.e., can have a spacing along the central axis (z).

Figure 4C:
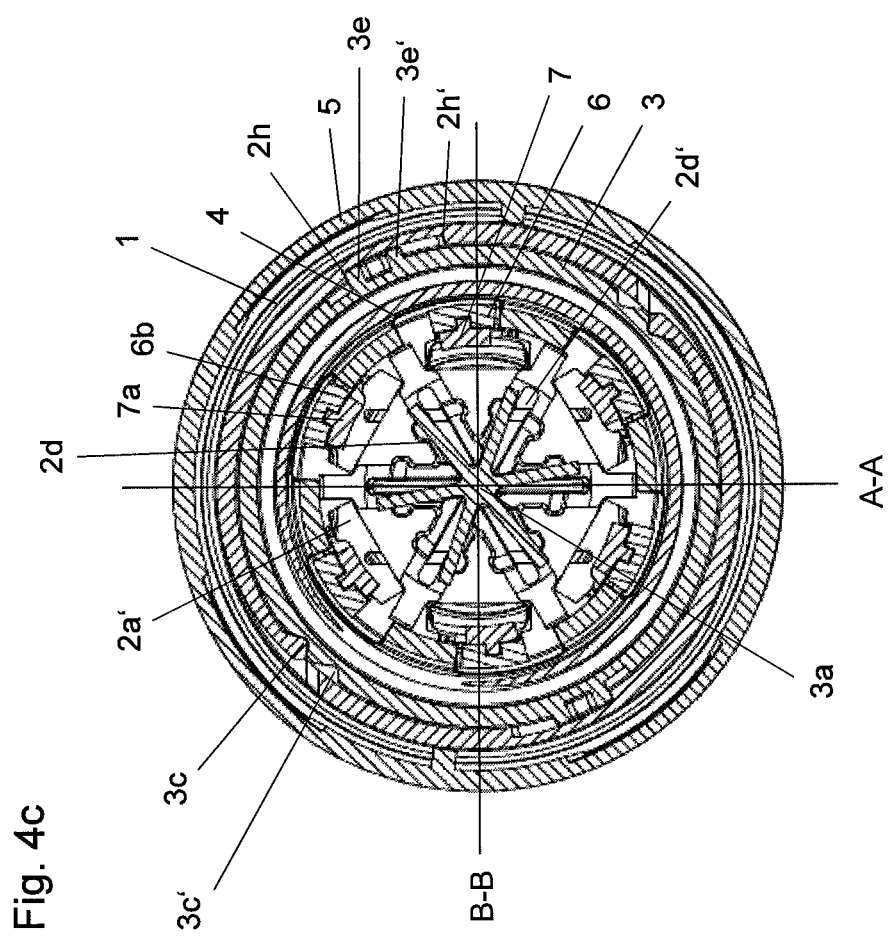
FIG. 4c shows a cross-sectional view of the embodiment of the insertion device in a loaded position according to FIG. 4a, the cross-sectional view corresponding to the section line D-D drawn in FIG. 8.
Figure 4E:
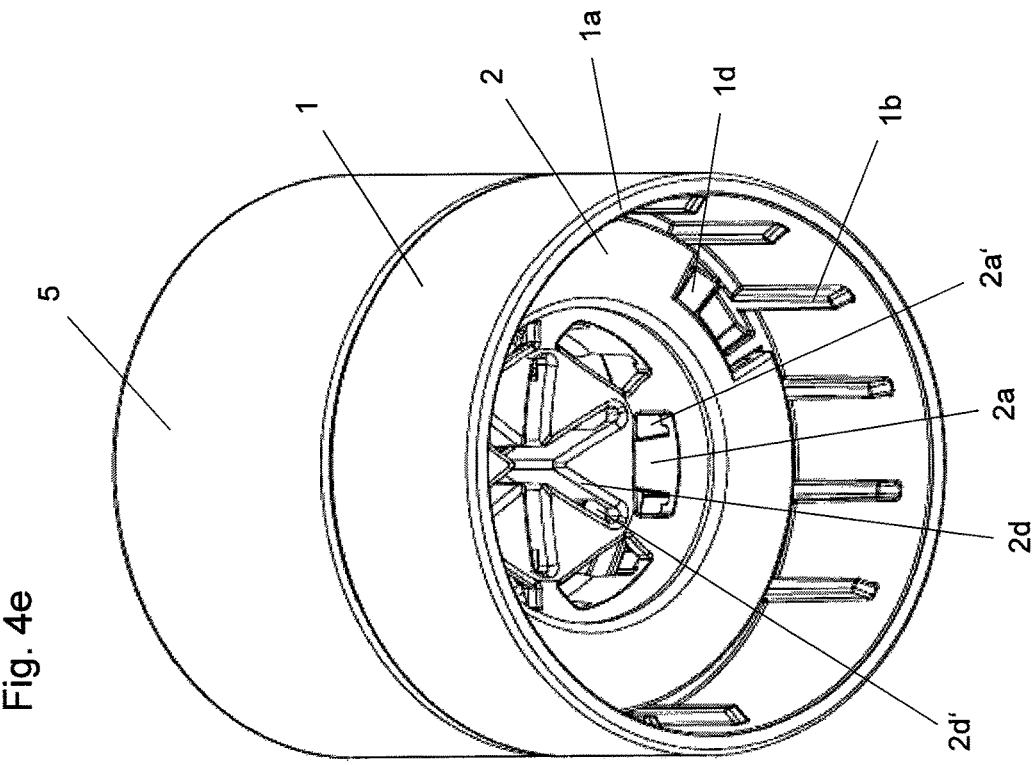
Figure 4D:
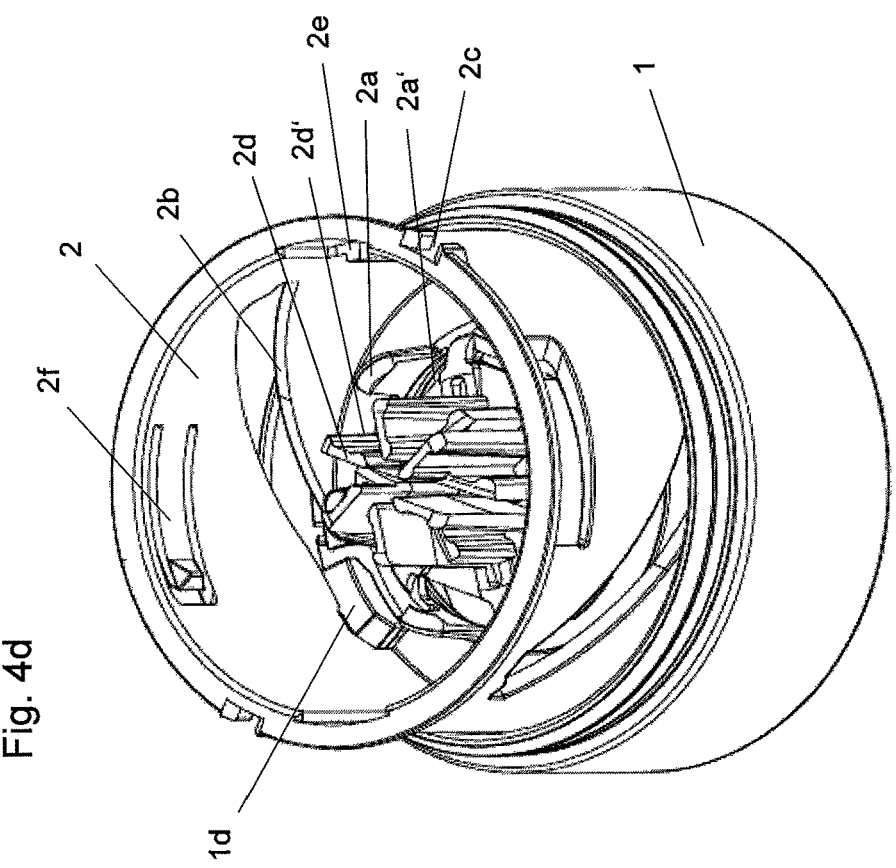

FIG. 4a represents a longitudinal sectional view of the insertion device in a loaded position, the longitudinal sectional view corresponding to the section line A-A drawn in FIG. 4c. FIG. 4b shows the insertion device according to FIG. 4a, the longitudinal sectional view corresponding to the section line B-B drawn in FIG. 4c. The patient rotates the head part (5) relative to the base part (1) of the insertion device in the first rotational direction. The guide cam track (2b) of the retaining element (2) is guided by the guide cams (1d) arranged on the base part (1) in such a manner that the retaining element (2) is moved along the central axis (z) relative to the base part (1) from the distal position into the proximal position. As can be seen in FIGS. 4d and 4e, the guide cam (1d) of the base part (1) comes into stopping contact with the distal end of the guide cam track (2b) of the retaining element (2). The distal end of the guide cam track (2b) of the retaining element (2) and the guide cam (1d) of the base part (1) are constructed such that the guide cam (1d) of the base part (1) can hold the retaining element (2) in the proximal position. The sliding element stop (3b) of the sliding element (3) rests against the retaining element stop (2e) of the retaining element (2), so that the sliding element (3) is moved along with the retaining element (2) into the proximal position. The sliding element (3) moves the pushbutton (7) via the sliding element edge (3f) of the sliding element (3) and via the pushbutton incline (7d) of the pushbutton. The snap hook (7b) of the pushbutton (7) comes into stopping contact with the distal end of the cover ridge (6b) of the cover (6). The spring (4), which is mounted between the sliding element (3) and the cover (6), is cocked, or further cocked, in the process.

Figure 5C:
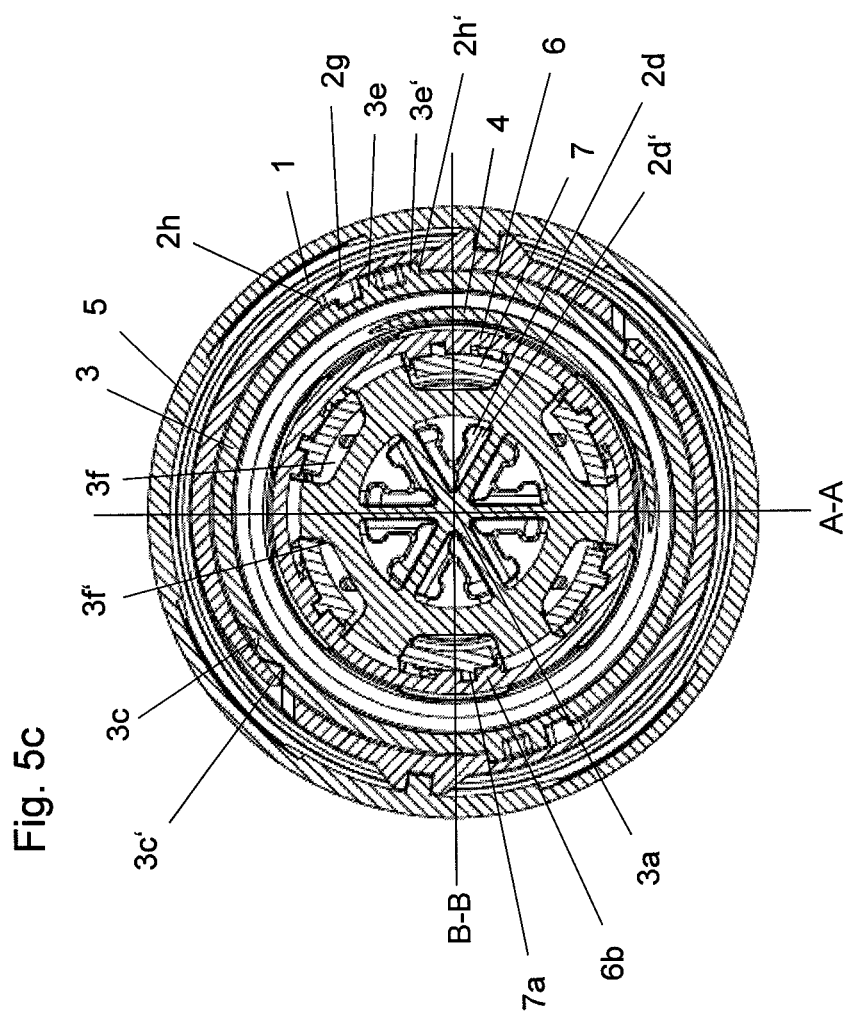
FIG. 5c shows a cross-sectional view of the embodiment of the insertion device in the triggered position according to FIG. 5a, the cross-sectional view corresponding to the section line E-E drawn in FIG. 9.

FIG. 5a represents a longitudinal sectional view of the embodiment of the insertion device in a triggered position, the longitudinal sectional view corresponding to the section line A-A drawn in FIG. 5c. FIG. 5b shows the insertion device according to FIG. 5a, the longitudinal sectional view corresponding to the section line B-B drawn in FIG. 5c. The patient presses the pushbutton (7) in the distal direction. The pushbutton incline (7d) of the pushbutton (7) cooperates with the sliding element edge (3f) of the sliding element opening (3f) of the sliding element (3) in such a manner that the sliding element (3) is rotated relative to the retaining element (2), preferably by an angle of rotation of approximately 10°. FIGS. 2c, 4c and 5c respectively show the angle of rotation displacement between the sliding element (3) and the retaining element (2) in the initial position, the loaded position of the insertion device and in the triggered position of the insertion device. When the insertion device is triggered, the snapper (2f) of the retaining element (2) comes to rest in the second longitudinal groove (3c') of the sliding element (3). The sliding element stop (3b) of the sliding element (3) comes out of stopping contact with the retaining element stop (2e) of the retaining element (2). The first and second sliding element ridges (3e, 3e') of the sliding element are in a guiding engagement with the guide groove (2g) of the retaining element (2) in such a manner that the sliding element (3) can be moved relative to the retaining element (2) via the spring force of the cocked spring (4). In the process, the striking element (3a) of the sliding element (3) strikes with the aid of the spring force of the spring (4) against the retaining tab (8b) of the infusion set (8), or presses on this retaining tab (8b), such that the retaining wings (8a) of the infusion set (8) snap out of the retaining arms (2a) of the retaining element (2), the infusion set (8) is moved distally and thereby the infusion set can puncture the patient's skin with the cannula (8c) provided on the infusion set.

Figure 6A:
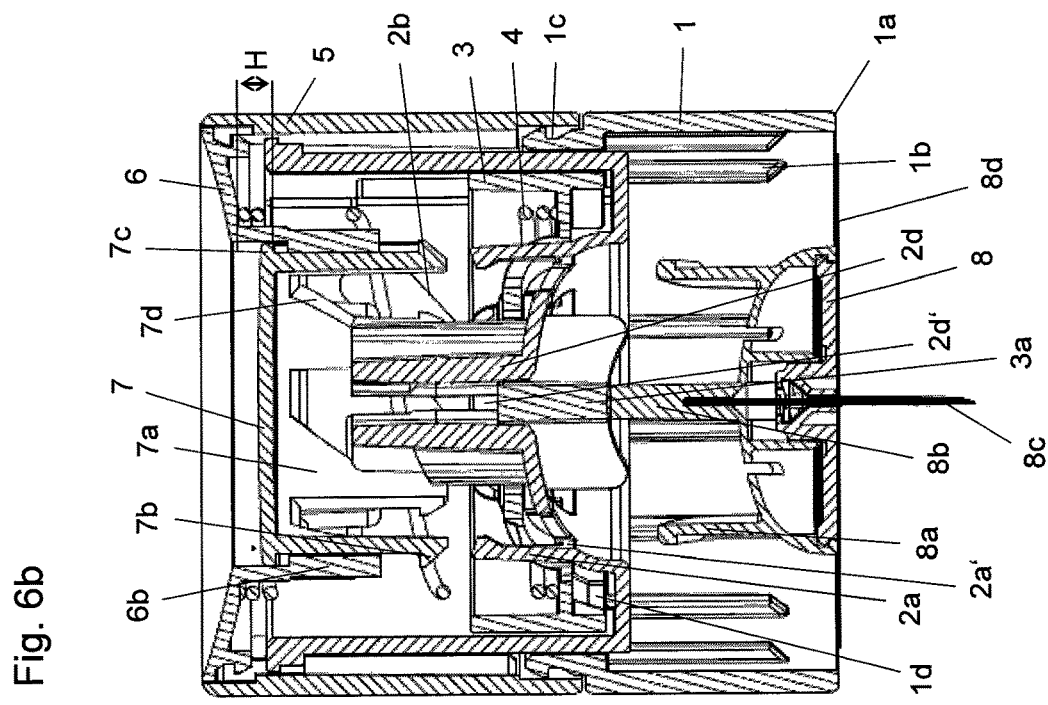
FIG. 6a shows a longitudinal sectional view of the embodiment of the insertion device with an infusion set having punctured the skin of a patient, the longitudinal sectional view corresponding to the section line A-A drawn in FIG. 5c.
Figure 6B:
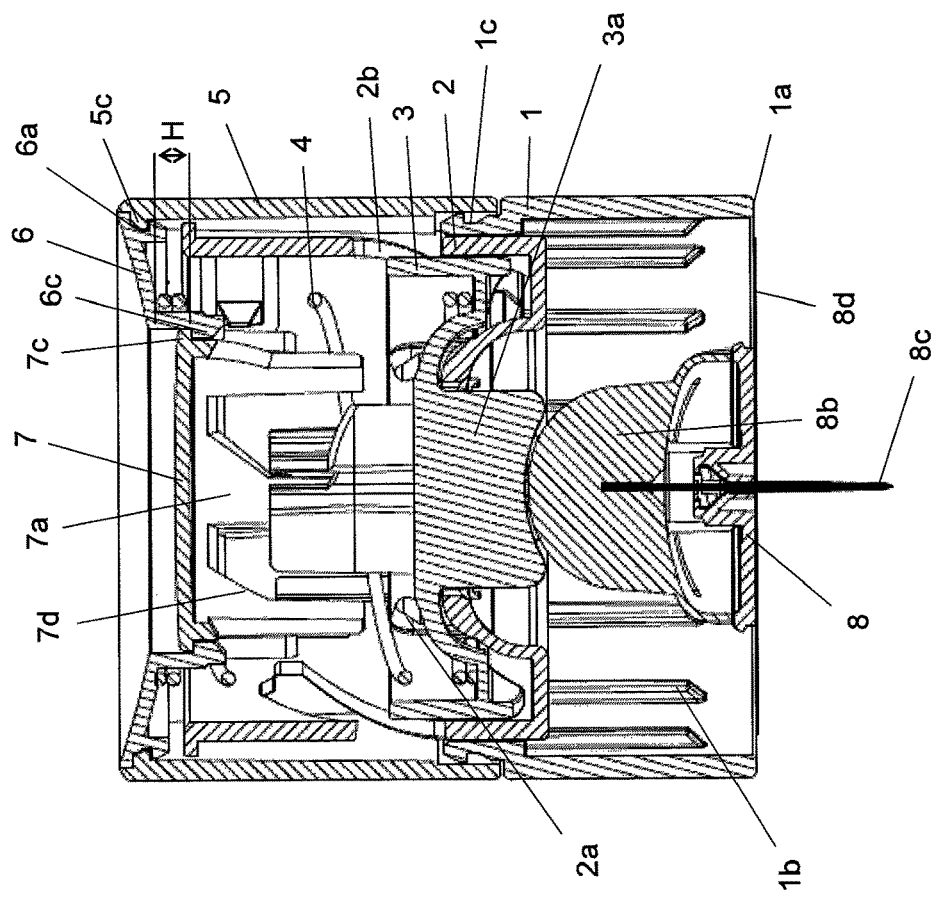
FIG. 6b shows a longitudinal sectional view of the embodiment of the insertion device according to FIG. 6a with the infusion set having punctured the skin of the patient, the longitudinal sectional view corresponding to the section line B-B drawn in FIG. 5c.
Figure 6C:
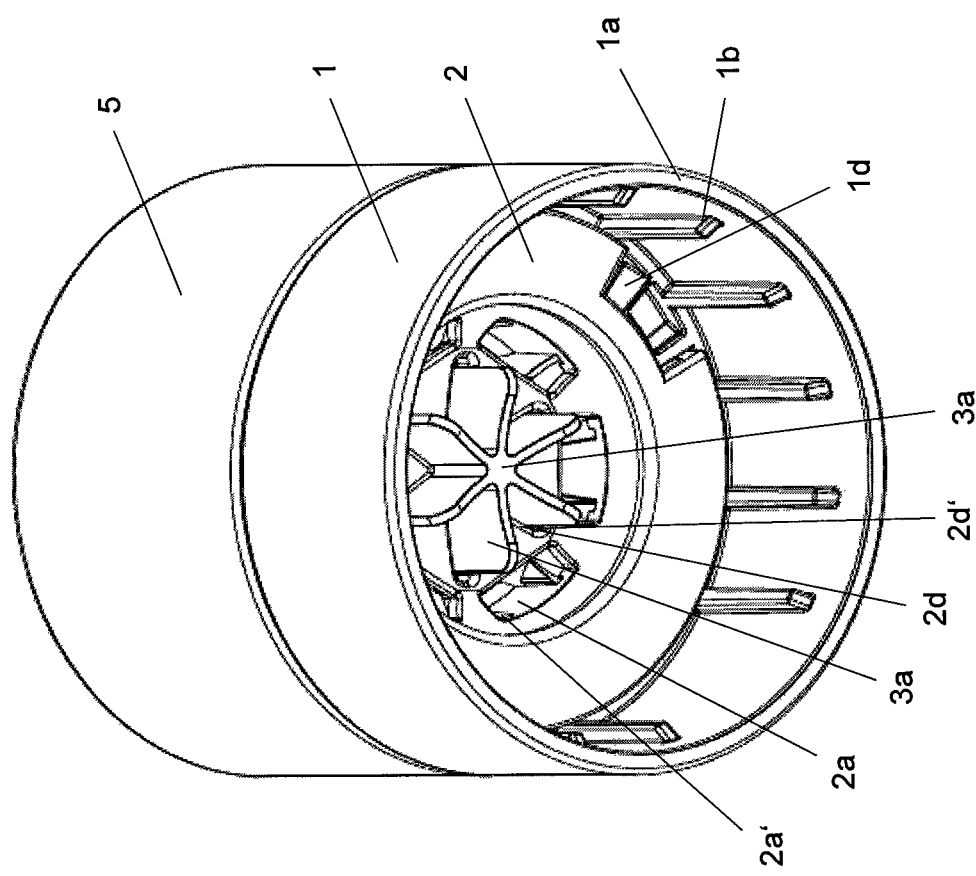
FIG. 6c, wherein the head part (5), the base part (1), the sliding element (3) and the retaining element are visible, shows a detail view of the embodiment of the insertion device according to FIG. 6a with the infusion set having punctured the skin of the patient.

FIG. 6a shows a longitudinal sectional view of the insertion device with an infusion set having punctured the skin of a patient, the longitudinal sectional view corresponding to the section line A-A drawn in FIG. 6c. FIG. 6b shows the insertion device according to FIG. 6a, the longitudinal sectional view corresponding to the section line B-B drawn in FIG. 6c. The cannula (8c) of the infusion set (8) has punctured the patient's skin. The pushbutton disc (7c) of the pushbutton (7) is in stopping contact with the cover shoulder (6c) of the cover (6). The sliding element (3) comes into stopping contact with the guide cam (1d) of the base part (1). The striking element (3a) of the sliding element (3) is out of stopping contact with the retaining tab (8b) of the infusion set (8). As can be seen in FIG. 6c, the striking element (3a) of the sliding element (3) protrudes through the guide slot (2d') of the retaining element (2). The spring (4), which is mounted between the cover (6) and the sliding element (3), is relaxed. The insertion device can now be removed from the patient's skin, the infusion set (8) remaining in place on the patient's skin by means of the adhesive bandage (8d) provided on the infusion set.

In order to bring the insertion device back into the initial position according to FIGS. 2a and 2b, the patient turns the head part (5) in the second rotational direction relative to the base part (1) of the insertion device. The guide cam track (2b) of the retaining element (2) is guided by the guide cam (1d) arranged on the base part (1) in such a manner that the retaining element (2) is moved along the central axis (z) relative to the base part (1) from the proximal position into the distal position. The guide cam (1d) of the base part (1) comes into stopping contact with the proximal end of the guide cam track (2b) of the retaining element (2). The proximal end of the guide cam track (2b) of the retaining element (2), the guide cam (1d) of the base element (1) and the control cam track (3d) of the sliding element (3) are designed such that the sliding element (3) can be rotated relative to the retaining element (2), preferably by the angle of rotation of approximately 10°. The retaining element (2) is in the distal position, so that a new infusion set (8) can be inserted into the insertion device.

The invention claimed is:

1. An insertion device for an infusion set, comprising:
   an advancement unit for moving the infusion set along a central axis of the insertion device from a proximal position of the insertion device into a distal position of the insertion device;
   a retaining element for retaining the infusion set, wherein the retaining element comprises a guide element;
   a base part accommodating the retaining element, wherein the base part comprises in a single component a mating guide element and a contact surface configured to be placed on an application point of a patient's body, the mating guide element being axially fixed relative to the contact surface; and
   a head part rotatably coupled to the base part such that the head part and the base part are rotatable relative to one another about the central axis,
   wherein the guide element of the retaining element is in a guiding engagement with the mating guide element of the base part and relative rotation between the head part and the base part in a first rotational direction causes the guide element of the retaining element to be rotatably guided with the mating guide element of the base part such that the retaining element rotates along the central axis relative to the base part from a distal position of the retaining element into a proximal position of the retaining element.

2. The device of claim 1, wherein the mating guide element is configured as a guide cam track and the guide element is configured as a guide cam.

3. The device of claim 1, wherein relative rotation between the head part and the base part in a second rotational direction causes the guide element to be guided with the mating guide such that the retaining element moves along the central axis relative to the base part from the proximal position of the retaining element into the distal position of the retaining element.

4. The device of claim 3, wherein the mating guide element is configured as a guide cam track and the guide element is configured as a guide cam.

5. The device of claim 1, wherein the advancement unit comprises an elastic means and a sliding element.

6. The device of claim 5, wherein the elastic means is caused to be cocked in response to relative rotation between the head part and the base part in the first rotational direction.

7. The device of claim 5, wherein the elastic means is supported on the sliding element and one of the head part, a cover or the base part.

8. The device of claim 5, wherein the elastic means is configured as a compression spring or as a tensile spring.

9. The device of claim 5, wherein in the proximal position of the insertion device, the sliding element is rotatable from a first position into a second position, wherein the sliding element is configured to be retained by the retaining element in the first position and to be released by the retaining element in the second position such that the sliding element is movable axially along the central axis relative to the retaining element.

10. The device of claim 5, wherein in the distal and in the proximal positions of the insertion device, the sliding element is arranged offset from the retaining element by an angle of rotation.

11. The device of claim 10, wherein the angle of rotation is approximately 10°.

12. The device of claim 5, wherein the sliding element comprises a striking element for knocking the infusion set out of the retaining element.

13. The device of claim 1, wherein the retaining element is rotationally fixedly connected to the head part.

14. The device of claim 1, wherein a cover is rotationally fixedly connected to the head part.

15. The device of claim 14, wherein a proximal end of the head part accommodates the cover.

16. The device of claim 14, wherein the cover accommodates a pushbutton.

17. The device of claim 16, wherein the pushbutton can be displaced by an actuating stroke along the central axis.

18. The device of claim 17, wherein the advancement unit comprises an elastic means and a sliding element, wherein in the proximal position of the insertion device, the sliding element is rotatable from a first position into a second position, wherein the sliding element is configured to be retained by the retaining element in the first position and to be released by the retaining element in the second position such that the sliding element is movable axially along the central axis relative to the retaining element, and wherein the pushbutton is configured such that when displaced by the actuation stroke, the sliding element rotates about the central axis relative to the retaining element by an angle of rotation into the second position.

19. An insertion device for an infusion set, comprising:
a retaining element for retaining the infusion set, wherein the retaining element comprises a guide element;
a base part comprising in a single component a mating guide element and a contact surface configured to be placed on an application point of a patient's body, the mating guide element being axially fixed relative to the contact surface;
a head part rotatably coupled to the base part such that the head part and the base part are rotatable relative to one another about a central axis;
a sliding element movable axially within an interior of the base part and the head part, the sliding element for moving the infusion set along the central axis; and
an actuator for causing the sliding element to move distally along the central axis from a loaded position into an insertion position,
wherein the guide element of the retaining element is in a rotatable guiding engagement with the mating guide element of the base part and relative rotation between the head part and the base part in a first rotational direction causes the retaining element to rotate along the central axis relative to the base part from a distal position of the retaining element into a proximal position of the retaining element and causes a guide element associated with the sliding element to be guided with the mating guide element of the base part such that the sliding element moves proximally along the central axis relative to the base part from an initial position into the loaded position.

20. The insertion device of claim 19, wherein in the loaded position, the sliding element is rotatable about the central axis from a first position into a second position, the sliding element prevented from axial movement in the first position and movable axially relative to the retaining element in the second position.

21. The insertion device of claim 20, wherein upon actuating the actuator in the loaded position, the sliding element rotates from the first position into the second position and the sliding element is caused to move axially into the insertion position such that the infusion set is inserted at the application point.

22. A method for inserting an infusion set using an insertion device, comprising:
receiving the insertion device, the insertion device comprising:
an advancement unit for moving the infusion set along a central axis from a proximal position into a distal position;
a retaining element for retaining the infusion set, wherein the retaining element comprises a guide element;
a base part accommodating the retaining element, wherein the base part comprises in a single component a mating guide element and a contact surface configured to be placed on an application point of a patient's body, the mating guide element being axially fixed relative to the contact surface;
a head part rotatably coupled to the base part such that the head part and the base part are rotatable relative to one another about the central axis;
and an actuator for causing the advancement unit to move the infusion set to the distal position when actuated,
wherein the guide element of the retaining element is in a rotatable guiding engagement with the mating guide element of the base part;
performing a relative rotational movement between the head part and the base part in a first direction;
inserting the infusion set into the retaining element;
performing a relative rotational movement between the head part and the base part in a second rotational direction such that the retaining element rotates along the central axis relative to the base part from a distal position of the retaining element into a proximal position of the retaining element;
placing the insertion device on the application point on the patient's body;
actuating the insertion device using the actuator; and
removing the insertion device from the application point on the patient's body.

* * * * *